United States Patent [19]
Olsen et al.

[11] Patent Number: 5,837,498
[45] Date of Patent: Nov. 17, 1998

[54] CORPUSCLES OF STANNIUS PROTEIN, STANNIOCALCIN

[75] Inventors: Henrik S. Olsen, Gaithersburg; Mark D. Adams, Potomac, both of Md.

[73] Assignee: Human Genome Scienes, Inc., Rockville, Md.

[21] Appl. No.: 208,005

[22] Filed: Mar. 8, 1994

[51] Int. Cl.$^6$ .............................. C12N 15/12; C12N 15/18
[52] U.S. Cl. .................. 435/69.4; 536/23.51; 435/320.1; 435/325
[58] Field of Search ................................ 536/23.5, 24.33, 536/23.1, 24.31; 435/6, 172.3, 69.1, 69.4, 240.2, 252.33, 320.1, 325

[56] References Cited

U.S. PATENT DOCUMENTS

| | | |
|---|---|---|
| 5,447,841 | 9/1995 | Gray et al. . |
| 5,491,224 | 2/1996 | Bittner et al. . |
| 5,538,869 | 7/1996 | Siciliano et al. . |
| 5,545,524 | 8/1996 | Trent et al. . |

FOREIGN PATENT DOCUMENTS

88/03949    6/1988    WIPO .

OTHER PUBLICATIONS

Olsen, H., et al.*PNAS*, 93:1792–1796, Mar. 1996.
Wagner, G.F. et al., *Journal of Bone and Mineral Research*, 12(2), 1997.
Haddad, M. et al.,*Endocrinology*, 137 (3):2113–2117, 1996.
Stern, P.H., et al., *J. Bone Mineral Res.*, 6(11):1153–60, 1991.
Butkus, A., et al., Purification and Cloning of a Corpuscles of Stannius Protein From *Anguilla australis*, Mol. Cell Endocrinol., 54:123–33 (1987), abstract only.
Lafeber, F.P. et al., Identification of hypocalcin (teleocalcin isolated from trout *Stannius corpuscles*, Gen. Comp. Endocrinol. 69:19–30 (1988), Abstract Only.
Milliken, C.E. et al., Effects of Synthetic peptide Fragments of teleocalcin (hypocaloin) on calcium uptake in juvenile rainbow trout (*Salmo gairdneri*), Gen. Comp. Endocrinol., 77:416–22 (1990), Abstract Only.
Wagner, G.F. et al., Molecular cloning and cDNA sequence analysis of coho salmon stanniocalcin, Mol. Cell. Endocrinol., 90:7–15 (1992), Abstract Only.

*Primary Examiner*—Marianne P. Allen
*Attorney, Agent, or Firm*—Elliot M. Olstein; J. G. Mullins

[57] ABSTRACT

There is disclosed a human Corpuscles of Stannius, stanniocalcin polypeptide and DNA(RNA) encoding such polypeptide. There is also provided a procedure for producing such polypepticle by recombinant techniques and for producing antibodies and antagonist/inhibitors against such polypeptide. Another aspect of the invention provides a combination of the polypeptide of the present invention and a suitable pharmaceutical carrier for providing therapeutic treatment of disease or the inhibition of such polypeptide for therapeutic treatment of disease.

24 Claims, 5 Drawing Sheets

FIG. 1A

```
GAAACTTCTCAGAGAATGCTCCAAAACTCAGCAGTGCTCTTCTGGTGCTGGTGATCAGTGCT
-----+---------+---------+---------+---------+---------+
            MetLeuGlnAsnSerAlaValLeuLeuValLeuValIleSerAla

TCTGCAACCCATGAGGCGGAGCAGAATGACTCTGTGAGCCCCAGGAAATCCCGAGTGGCG
-----+---------+---------+---------+---------+---------+
SerAlaThrHisGluAlaAlaGluGlnAsnAspSerValSerProArgLysSerArgValAla

GCCCAAAACTCAGCTGAAGTGGTTCGTTGCCTCAACAGTGCTCTACAGGTCGGCTGCGGG
-----+---------+---------+---------+---------+---------+
AlaGlnAsnSerAlaGluValValArgCysLeuAsnSerAlaLeuGlnValGlyCysGly

GCTTTTGCATGCCTGGAAAACTCCACCTGTGACACAGATGGGATGTATGACATCTGTAAA
-----+---------+---------+---------+---------+---------+
AlaPheAlaCysLeuGluAsnSerThrCysAspThrAspGlyMetTyrAspIleCysLys

TCCTTCTTGTACAGCGCTGCTAAATTTGACACTCAGGGAAAAGCATTCGTCAAAGAGAGC
-----+---------+---------+---------+---------+---------+
```

FIG. 1B

SerPheLeuTyrSerAlaAlaLysPheAspThrGlnGlyLysAlaPheValLysGluSer

TTAAAATGCATCGCCAACGGGGTCACCTCCAAGGTCTCTTCCTCGCCATTCGGAGGTGCTCC

LeuLysCysIleAlaAsnGlyValThrSerLysValPheLeuAlaIleArgArgCysSer

ACTTTCCAAAGGATGATTGCTGAGGTTGCAGGAAGAGTGCTACAGCAAGCTGAATGTGTGC

ThrPheGlnArgMetIleAlaGluValGlnGluGluCysTyrSerLysLeuAsnValCys

AGCATCGCCAAGCGGAACCCTGAAGCCATCACTGAGGTCGTCCAGCTGCCCAATCACTTC

SerIleAlaLysArgAsnProGluAlaIleThrGluValValGlnLeuProAsnHisPhe

TCCAACAGATACTATAACAGACTTGTCCGAAGCCTGCTGGAATGTGATGAAGACACAGTC

SerAsnArgTyrTyrAsnArgLeuValArgSerLeuLeuGluCysAspGluAspThrVal

FIG. 1C

```
AGCACAATCAGAGACAGCCTGATGGAGAAAATTGGGCCTAACATGGCCAGCCTCTTCCAC
+-------+-------+-------+-------+-------+-------+
  SerThrIleArgAspSerLeuMetGluLysIleGlyProAsnMetAlaSerLeuPheHis

ATCCTGCAGACAGACCACTGTGCCCAAACACACCCACGAGCTGACTTCAACAGGAGACGC
+-------+-------+-------+-------+-------+-------+
  IleLeuGlnThrAspHisCysAlaGlnThrHisProArgAlaAspPheAsnArgArgArg

ACCAATGAGCCGCAGAAGCTGAAAGTCCTCCTCAGGAACCTCCGAGGTGAGGAGGACTCT
+-------+-------+-------+-------+-------+-------+
  ThrAsnGluProGlnLysLeuLysValLeuLeuArgAsnLeuArgGlyGluGluAspSer

CCCTCCCACATCAAACGCACATCCCATGAGAGTGCATAACCAGGGAGAGGT
+-------+-------+-------+-------+-------+
  ProSerHisIleLysArgThrSerHisGluSerAla
```

FIG. 2

```
MLQNSAVLLVLVISASATHEAEQNDSVSPRKSRVAAQNSAEVVRCLNSALQVGCGAFACL
ML   +  V  ++  +A         +   SPR++R  ++  +   ++V RCLN AL VGCG FACL
MLAKFGLCAVFLVLGTAATFDTDPEEASPRRARFSSNSPSDVARCLNGALAVGCGTFACL

ENSTCDTDGMYDICKSFLYSAAKFDTQGKAFVKESLKCIANGVTSKVFLAIRRCSTFQRM
ENSTCDTDGM+DIC+ F ++AA F+TQGK FVKESL+CIANGVTSKVF   IRRC  FQRM
ENSTCDTDGMHDICQLFHTAATFNTQGKTFVKESLRCIANGVTSKVFQTIRRCGVFQRM

IAEVQEECYSKLNVCSIAKRNPEAITEVVQLPNHFSNRYYNRLVRSLLECDEDTVSTIRD
I+EVQEECYS+L++C +A+ NPEAI EVVQ+P HF NRYY+ L++SLL CDE+TV+ +R
ISEVQEECYSRLDICGVARSNPEAIGEVVQPAHFPNRYYSTLLQSLLACDEETVAVVRA

SLMEKIGPNMASLFHILQTDHCAQ
L+ ++GP+M +LF +LQ  HC Q
GLVARLGPDMETLFQLLQNKHCPQ 204
```

Human Protein of Stannius/Stanniocalcin

Expression and purification

M   MW Marker      2. 10λ
1. 15λ              3. 5λ

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 771 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
GAAACTTCTC   AGAGAATGCT   CCAAAACTCA   GCAGTGCTTC   TGGTGCTGGT   GATCAGTGCT     60
TCTGCAACCC   ATGAGGCGGA   GCAGAATGAC   TCTGTGAGCC   CCAGGAAATC   CCGAGTGGCG    120
GCCCAAAACT   CAGCTGAAGT   GGTTCGTTGC   CTCAACAGTG   CTCTACAGGT   CGGCTGCGGG    180
GCTTTTGCAT   GCCTGGAAAA   CTCCACCTGT   GACACAGATG   GGATGTATGA   CATCTGTAAA    240
TCCTTCTTGT   ACAGCGCTGC   TAAATTTGAC   ACTCAGGGAA   AAGCATTCGT   CAAAGAGAGC    300
TTAAAATGCA   TCGCCAACGG   GGTCACCTCC   AAGGTCTTCC   TCGCCATTCG   GAGGTGCTCC    360
ACTTTCCAAA   GGATGATTGC   TGAGGTGCAG   GAAGAGTGCT   ACAGCAAGCT   GAATGTGTGC    420
AGCATCGCCA   AGCGGAACCC   TGAAGCCATC   ACTGAGGTCG   TCCAGCTGCC   CAATCACTTC    480
TCCAACAGAT   ACTATAACAG   ACTTGTCCGA   AGCCTGCTGG   AATGTGATGA   AGACACAGTC    540
AGCACAATCA   GAGACAGCCT   GATGGAGAAA   ATTGGGCCTA   ACATGGCCAG   CCTCTTCCAC    600
ATCCTGCAGA   CAGACCACTG   TGCCCAAACA   CACCCACGAG   CTGACTTCAA   CAGGAGACGC    660
ACCAATGAGC   CGCAGAAGCT   GAAAGTCCTC   CTCAGGAACC   TCCGAGGTGA   GGAGGACTCT    720
CCCTCCCACA   TCAAACGCAC   ATCCCATGAG   AGTGCATAAC   CAGGGAGAGG   T             771
```

( 2 ) INFORMATION FOR SEQ ID NO:2:

( i ) SEQUENCE CHARACTERISTICS:
        ( A ) LENGTH: 247 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met  Leu  Gln  Asn  Ser  Ala  Val  Leu  Leu  Val  Leu  Val  Ile  Ser  Ala
               -30                 -25                 -20
Ser  Ala  Thr  His  Glu  Ala  Glu  Gln  Asn  Asp  Ser  Val  Ser  Pro  Arg
               -15                 -10                  -5
Lys  Ser  Arg  Val  Ala  Ala  Gln  Asn  Ser  Ala  Glu  Val  Val  Arg  Cys
                1                   5                  10
Leu  Asn  Ser  Ala  Leu  Gln  Val  Gly  Cys  Gly  Ala  Phe  Ala  Cys  Leu
               15                  20                  25
Glu  Asn  Ser  Thr  Cys  Asp  Thr  Asp  Gly  Met  Tyr  Asp  Ile  Cys  Lys
               30                  35                  40
Ser  Phe  Leu  Tyr  Ser  Ala  Ala  Lys  Phe  Asp  Thr  Gln  Gly  Lys  Ala
               45                  50                  55
Phe  Val  Lys  Glu  Ser  Leu  Lys  Cys  Ile  Ala  Asn  Gly  Val  Thr  Ser
               60                  65                  70
```

```
Lys  Val  Phe  Leu  Ala  Ile  Arg  Arg  Cys  Ser  Thr  Phe  Gln  Arg  Met
          75                       80                      85

Ile  Ala  Glu  Val  Gln  Glu  Glu  Cys  Tyr  Ser  Lys  Leu  Asn  Val  Cys
          90                       95                     100

Ser  Ile  Ala  Lys  Arg  Asn  Pro  Glu  Ala  Ile  Thr  Glu  Val  Val  Gln
         105                      110                     115

Leu  Pro  Asn  His  Phe  Ser  Asn  Arg  Tyr  Tyr  Asn  Arg  Leu  Val  Arg
         120                      125                     130

Ser  Leu  Leu  Glu  Cys  Asp  Glu  Asp  Thr  Val  Ser  Thr  Ile  Arg  Asp
         135                      140                     145

Ser  Leu  Met  Glu  Lys  Ile  Gly  Pro  Asn  Met  Ala  Ser  Leu  Phe  His
         150                      155                     160

Ile  Leu  Gln  Thr  Asp  His  Cys  Ala  Gln  Thr  His  Pro  Arg  Ala  Asp
         165                      170                     175

Phe  Asn  Arg  Arg  Arg  Thr  Asn  Glu  Pro  Gln  Lys  Leu  Lys  Val  Leu
         180                      185                     190

Leu  Arg  Asn  Leu  Arg  Gly  Glu  Glu  Asp  Ser  Pro  Ser  His  Ile  Lys
         195                      200                     205

Arg  Thr  Ser  His  Glu  Ser  Ala
         210
```

( 2 ) INFORMATION FOR SEQ ID NO:3:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

GACTGCATGC TCCAAAACTC AGCAGTG      27

( 2 ) INFORMATION FOR SEQ ID NO:4:

( i ) SEQUENCE CHARACTERISTICS:
        ( A ) LENGTH: 31 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GACTAGATCT TGCACTCTCA TGGGATGTGC G      31

( 2 ) INFORMATION FOR SEQ ID NO:5:

( i ) SEQUENCE CHARACTERISTICS:
        ( A ) LENGTH: 204 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:5:

```
Met  Leu  Ala  Lys  Phe  Gly  Leu  Cys  Ala  Val  Phe  Leu  Val  Leu  Gly
                    5                       10                      15

Thr  Ala  Ala  Thr  Phe  Asp  Thr  Asp  Pro  Glu  Glu  Ala  Ser  Pro  Arg
                   20                       25                      30

Arg  Ala  Arg  Phe  Ser  Ser  Asn  Ser  Pro  Ser  Asp  Val  Ala  Arg  Cys
```

-continued

| | | | | 35 | | | | 40 | | | | 45 |
|---|---|---|---|---|---|---|---|---|---|---|---|---|
| Leu | Asn | Gly | Ala | Leu 50 | Ala | Val | Gly | Cys | Gly 55 | Thr | Phe | Ala | Cys | Leu 60 |
| Glu | Asn | Ser | Thr | Cys 65 | Asp | Thr | Asp | Gly | Met 70 | His | Asp | Ile | Cys | Gln 75 |
| Leu | Phe | Phe | His | Thr 80 | Ala | Ala | Thr | Phe | Asn 85 | Thr | Gln | Gly | Lys | Thr 90 |
| Phe | Val | Lys | Glu | Ser 95 | Leu | Arg | Cys | Ile | Ala 100 | Asn | Gly | Val | Thr | Ser 105 |
| Lys | Val | Phe | Gln | Thr 110 | Ile | Arg | Arg | Cys | Gly 115 | Val | Phe | Gln | Arg | Met 120 |
| Ile | Ser | Glu | Val | Gln 125 | Glu | Glu | Cys | Tyr | Ser 130 | Arg | Leu | Asp | Ile | Cys 135 |
| Gly | Val | Ala | Arg | Ser 140 | Asn | Pro | Glu | Ala | Ile 145 | Gly | Glu | Val | Val | Gln 150 |
| Val | Pro | Ala | His | Phe 155 | Pro | Asn | Arg | Tyr | Tyr 160 | Ser | Thr | Leu | Leu | Gln 165 |
| Ser | Leu | Leu | Ala | Cys 170 | Asp | Glu | Glu | Thr | Val 175 | Ala | Val | Val | Arg | Ala 180 |
| Gly | Leu | Val | Ala | Arg 185 | Leu | Gly | Pro | Asp | Met 190 | Glu | Thr | Leu | Phe | Gln 195 |
| Leu | Leu | Gln | Asn | Lys 200 | His | Cys | Pro | Gln | | | | | | |

CORPUSCLES OF STANNIUS PROTEIN, STANNIOCALCIN

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human Corpuscles of Stannius protein. The invention also relates to inhibiting the action of such polypeptide.

Stanniocalcin (formerly known as both teleocalcin and hypocalcin) is an anti-hypercalcemic, glycoprotein hormone that is produced by the Corpuscles of Stannius, endocrine glands which are confined to bony fishes. The polypeptide of the present invention has a high degree of homology at the amino acid level to the glycoprotein hormone from fish which is involved in the regulation of calcium levels.

The Corpuscles of Stannius protein of non-humans has been studied extensively. Recently, a Corpuscles of Stannius protein has been purified and cloned from *Anguilla australis*. The kidneys of teleost fish have been found to contain secretory granules, the Corpuscles of Stannius. Electron microscopy indicates that the granules are of a proteinaceous nature and may represent hormones or enzymes of unrecognized physiological and biochemical function (Butkus, A. et al. Mol. Cell Endocrinol, 54:123–33 (1987)).

There has also been isolated and purified a glycoprotein from the Corpuscles of Stannius of trout, which is considered hypocalcin, the major hypocalcemic hormone of fish. This product is present in relatively large amounts in the Corpuscles of Stannius of several species (i.e., European eel, tilapia goldfish, and carp). Hypocalcin is typically released from the Corpuscles of Stannius in response to an experimentally induced increase of the blood calcium concentration. Ultrastructural observations show that after this treatment the hypocalcin-producing cell type of the corpuscles of stannius are almost completely degranulated. The isolated glycoprotein has an apparent molecular weight of 54 Kda. (Lafeber F. P. et al., Gen Comp. Endocrinol, 69:19–30 (1988)).

Moreover, it has recently been shown that several synthetic peptide fragments of teleocalcin inhibit calcium uptake in juvenile rainbow trout (*Salmo Gairdneri*). The N-terminal peptides (amino acids 1 to 20) of both eel and salmon teleocalcin significantly inhibit $Ca^{45}$ uptake at the high point of the calcium uptake cycle (up to 75%), although the effective doses of the peptides on a molar basis were 20 to 200 times that of the intact molecule. In contrast, the C-terminal fragment of eel teleocalcin (amino acids 202 to 231) did not have an inhibitory effect on calcium uptake (Milliken C. E. et al., Gen. Comp. Endocrinol, 77:416–22 (1990)).

There has also been a description of the purification and characterization of two salmon stanniocalcins, and the examination of the regulation of hormone secretion in response to calcium using both in vitro and in vivo model systems. The molecular cloning and cDNA sequence analysis of a coho salmon stanniocalcin messenger RNA (mRNA) from a salmon CS lambda gt10 cDNA library is described. The stanniocalcin mRNA in salmon is approximately 2 Kda in length and encodes a primary translation product of 256 amino acids. The first 33 residues comprise the preprotein region of the hormone, whereas the remaining 223 residues make up the mature form of the hormone. (Wagner G. F. et al., Mol. Cell Endocrinol, 90:7–15.(1992)).

In accordance with one aspect of the present invention, there is provided a novel mature polypeptide which is a Corpuscles of Stannius protein, as well as fragments, analogs and derivatives thereof. The Corpuscles of Stannius protein of the present invention is of human origin.

In accordance with another aspect of the present invention, there are provided polynucleotides (DNA or RNA) which encode such polypeptides.

In accordance with yet a further aspect of the present invention, there is provided a process for producing such a polypeptide by recombinant techniques.

In accordance with yet a further aspect of the present invention, there is provided a process for utilizing such polypeptide, or polynucleotide encoding such polypeptide for therapeutic purposes, for example, treatment of electrolyte disorders which lead to renal, bone and heart diseases, and disorders due to elevated bone resorption, e.g. osteoporosis and Paget's disease.

In accordance with yet a further aspect of the present invention, there is provided an antibody against such polypeptide. Such antibodies may be used in the treatment of hypocalcemia resulting in tetany, convulsions and other related disorders. Hypocalcemia can arise from a number of different causes including renal failure, hyperparathyroidism, severe infections or burns which traps calcium from the intercellular fluid and from pancreatic insufficiency.

In accordance with yet another aspect of the present invention, there are provided antagonist/inhibitors to such polypeptide, which may be used to inhibit the action of such polypeptide, for example, in the treatment of hypocalcemia and osteoporosis.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE DRAWINGS

FIG. 1 displays the cDNA sequence and corresponding deduced amino acid sequence of the preprocessed Corpuscles of Stannius protein. The amino acid sequence is shown below using the standard 3 letter abbreviation code.

FIG. 2 displays the comparison of the polypeptide sequence of the human stanniocalcin (upper line) to the stanniocalcin isolated from *Oncorhynchus kisutch* (lower line) (SEW ID NO:5). No apparent sequence homology exists beyond amino acid 204 of the stanniocalcin from Oncorhynchus kisutch. Total length of stanniocalcin isolated from Oncorhynchus kisutch is 256 amino acids.

Figure 3:
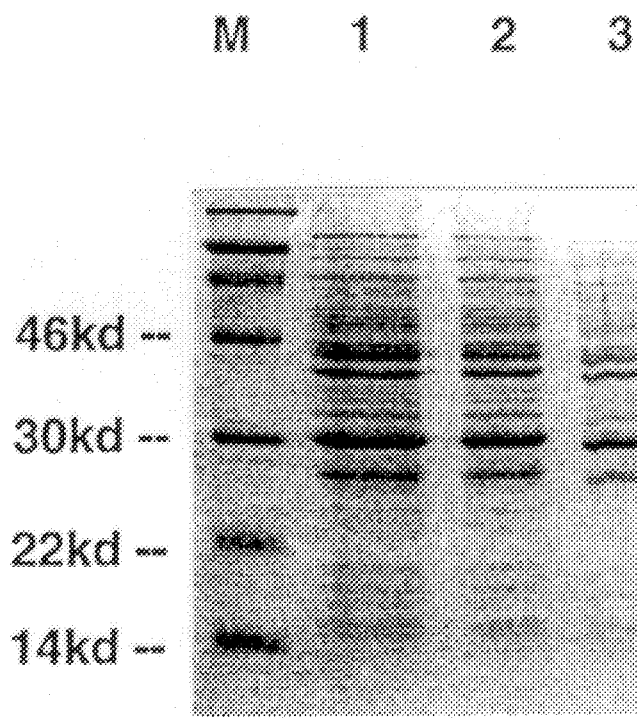
FIG. 3 shows the banding pattern of the human stanniocalcin polypeptide following bacterial expression and purification.

In accordance with one aspect of the present invention, there is provided an isolated nucleic acid (polynucleotide) which encodes for the mature polypeptide having the deduced amino acid sequence of FIG. 1 (SEQ ID NO:2), or for the mature polypeptide encoded by the cDNA of the clone deposited in the American Type Culture Collection, 12301 Park Lawn Drive, Rockville, Md. 20852 USA as ATCC Deposit No. 75652 on Jan. 25, 1994. The polynulcleotide sequence of FIG. 1 (SEQ ID NO:5) contains a presequence consisting of the first 15 nucleotides. The polynucleotide sequence encodes a translation product of 247 amino acids of which the first 33 amino acids may represent a prepro region of the protein. Thus, cleavage of the prepro region results in a mature active polypeptide of 214 amino acids.

The polynucleotide of the present invention was isolated from a human early stage lung cDNA library. It contains an open reading frame encoding a prepropolypeptide of 247 amino acids. The polypeptide has a high degree of homology to Stanniocalcin from *Anguilla australis,* 119 identical amino acids (61%) in a 195 amino acid overlap. It also has a very high homology to stanniocalcin from Oncorhynchus kisutch, 118 identical amino acids (57%) in a 204 amino acid overlap.

The polynucleotide of the present invention may be in the form of RNA or in the form of DNA, which DNA includes cDNA, genomic DNA, and synthetic DNA. The DNA may be double-stranded or single-stranded and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same, mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID NO:1) or the deposited cDNA.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a Corpuscles of Stannius polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Corpuscles of Stannius genes. The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as they are replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Salmonella typhimurium; Streptomyces; fungal cells, such as yeast; insect cells, such as Drosophila or Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBs, pD10, phagescript, PsiX174, Pbluescript SK, Pbsks, pNH8a, pNH16a, pNH18a, pNH46a (Stratagene); pTrc99A, pKK223-3, pKK233-3, pDR540, pRIT5 (Pharmacia). Eukaryotic: PWLNEO, pSV2cat, pOG44, pXT1, PSG (Stratagene) pSVK3, PBPV, PMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, (Cold Spring Harbor, N.Y., 1989), the disclosure of which is hereby incorporated by reference.

Transcription of the DNA encoding the polypeptide of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Corpuscles of Stannius protein is recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The polypeptide of the present invention may be used for therapeutic treatment of numerous electrolyte-based diseases. One cause of arterial hypertension is abnormal $Na^+$ transport across the cell wall of the vascular smooth cells due to a defect. in or inhibition of the Na-K pump, another is increased permeability to $Na^+$ as has been described in some forms of human hypertension. The net result is increases in intracellular $Na^+$, which makes the cell more sensitive to vasoconstrictive agents. Since $Ca^{++}$ follows $Na^+$, it is postulated that it is the accumulation of intracellular $Ca^{++}$ and not $Na^+$ per se that is responsible for increased sensitivity to sympathetic stimulation. Accordingly, since Corpuscles of Stannius protein can function as a hypocalcemic agent it can help to offset this increased intracellular $Ca^{++}$ and reduce or prevent hypertension. Further, hypercalcemia has been implicated in heart dysrhythmias, coma and cardiac arrest. Accordingly, the Corpuscles of Stannius protein may have therapeutic value for the treatment of these disorders by lowering the concentration of free calcium.

Hypertension is also directly related to renal disorders. Accordingly, a higher or lower than normal concentration of electrolytes can cause renal malfunction and directly lead to other more serious disorders. As an example calcium-phosphorus imbalance can cause muscle and bone pain, demineralization of the bones and calcification in various organs including the brain, eyes, myocardium and blood vessels. Accordingly, the polypeptide of the present invention may be used to offset disorders that are due to a calcium-phosphate imbalance. Renal failure itself leads to an abnormally high concentration of phosphate in the blood which can be reduced to normal concentrations by the polypeptide of the present invention.

The polypeptide of the present invention is also useful for the treatment of certain bone diseases. For example, excessive concentrations of calcium lead to the development of fibrous nodules in affected bone.

The causes of hypercalcemia may also be a number of different disorders including hyperparathyroidism, hypervitaminosis D, tumors that raises the serum calcium levels by destroying bone, sarcoidosis, hyperthyroidism, adrenal insufficiency, loss of serum albumin secondary to renal diseases, excessive GI calcium absorption and elevated concentration of plasma proteins. Accordingly, Corpuscles of Stannius protein is effective in reducing hypercalcemia and its related disorders.

Corpuscles of Stannius protein may also be useful for the treatment of other disorders relating to unusual electrolyte concentrations and fluid imbalance, for example, migraine headaches.

The polypeptide may also be employed in accordance with the present invention by expression of such polypeptide in vivo, which is often referred to as "gene therapy."

Thus, for example, cells from a patient may be engineered with a polynucleotide (DNA or RNA) encoding the polypeptide ex vivo, with the engineered cells then being provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of the polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

The pharmaceutical compositions may be administered in a convenient manner such as by the oral, intravenous, intraperitoneal, intramuscular, subcutaneous, intranasal, or intradermal routes. The amounts and dosage regimens administered to a subject will depend on a number of factors such as the mode of administration, the nature of the condition being treated, the body weight of the subject being treated and the judgment of the prescribing physician. Generally, they are given, for example, in therapeutically effective doses of at least about 0.1 mg/kg body weight and in most cases will not be administered in an amount in excess of about 10.0 mg/kg body weight, and preferably is given in doses of about 0.1 mg/kg body weight to about 1.0 mg/kg body weight daily, for several days, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting Corpuscles of Stannius protein in vivo by use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptide of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of Corpuscles of Stannius protein.

The antisense RNA oligonucleotide hybridizes to the mRNA in vivo and blocks translation of the mRNA molecule into the Corpuscles of Stannius protein (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures known in the art such that the antisense RNA or DNA may be expressed in vivo to inhibit production of Corpuscles of Stannius protein in the manner described above.

Accordingly, antisense constructs of Corpuscles of Stannius protein can be used to treat hypocalcemia by inactivating Corpuscles of Stannius protein and therefore preventing a hypocalcemic effect. Osteoporosis, characterized by thin and brittle bones due to a low level of calcium, can be treated by the above-described antisense constructs. In a similar manner these antisense constructs may be used to treat Paget's disease.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, CDR grafted single chain and humanized antibodies, as well as Fab fragments, or the product of an Fab expression library. Various procedures known in the art may be used for the production of such antibodies and fragments.

Antibodies generated against the polypeptide corresponding to a sequence of the present invention or its in vivo receptor can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies specific to the polypeptide of the present invention may further be used to inhibit the proper functioning of the polypeptide. In this manner, the antibodies may be used as antihypocalcemic agents by preventing the hypocalcemic function of the protein of stanniocalcin. Among the diseases which may be treated with these antibodies is osteoporosis.

The present invention is also directed to antagonist/inhibitors of the polypeptides of the present invention. The antagonist/inhibitors are those which inhibit or eliminate the function of the polypeptide.

Thus, for example, antagonists can bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to the catalytic site of the polypeptide thereby making it inaccessible to substrate and preventing biological activity. Examples, of small molecule inhibitors include but are not limited to small peptides or peptide-like molecules.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of Corpuscles of Stannius protein, since receptor sites are occupied. In these ways, the action of the Corpuscles of Stannius protein is prevented and the antagonist/inhibitors may be used as anti-hypocalcemic agents, to treat osteoporosis among other disorders where an increase in calcium levels is desired.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Corpuscles of Stannius Protein

The DNA sequence encoding for Corpuscles of Stannius Protein (ATCC #75652) is initially amplified using PCR oligonucleotide primers corresponding to the 5' and 3' sequences of Corpuscles of Stannius Protein and additional nucleotides corresponding to SphI restriction site and BglI were added to the 5' and 3' sequences respectively. The 5' oligonucleotide primer has the sequence 5'-GACTGCATGCTCCAAAACTCAGCAGTG-3' (SEQ ID NO:3), contains a SphI restriction enzyme site (GCATGC) and 21 nucleotides of Corpuscles of Stannius Protein coding sequence starting from the initiation codon; The 3' sequence 3'-GACTAGATCTTGCACTCTCATGGGATGTGCG-5' (SEQ ID NO:4) contains complementary sequences to Bgl II restriction site (AGATCT) and the last 21 nucleotides of Corpuscles of Stannius Protein coding sequence. The restriction enzyme sites correspond to the restriction enzyme sites on the bacterial expression vector pQE70 (Qiagen, Inc. 9259 Eton Ave., Chatsworth, Calif. 91311). pQE70 encodes antibiotic resistance (Amp$^r$), a bacterial origin of replication (ori), an IPTG-regulatable promoter operator (P/O), a ribosome binding site (RBS), a 6-His tag and restriction enzyme sites. pQE70 was then digested with SphI and Bgl II restriction enzymes. The amplified sequences were ligated into pQE70 and were inserted in frame with the sequence encoding for the histidine tag and the RBS. The ligation mixture was then used to transform E. coli strain M15/rep4 available from Qiagen under the trademark M15/rep 4. M15/rep4 contains multiple copies of the plasmid pREP4, which expresses the laci repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells were grown to an optical density 600 (O.D.$^{600}$) of between 0.4 and 0.6. IPTG (Isopropyl-B-D-thiogalacto pyranoside) was then added to a final concentration of 1 mM. IPTG induces by inactivating the laci repressor, clearing the P/O leading to increased gene expression. Cells were grown an extra. 3 to 4 hours. Cells were then harvested by centrifugation (20 mins at 6000×g). The cell pellet was solubilized in the chaotropic agent 6 Molar Guanidine HCl. After clarification, solubilized stanniocalcin was purified from this solution by chromatography on a Nickel-Chelate column under conditions that allow for tight binding by proteins containing the 6-His tag. (Hochuli, E. et al., Genetic Engineering, Principles & Methods, 12:87–98 (1990). Protein renaturation out of GnHCl can be accomplished by several protocols. (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The purified protein was analyzed by SDS-PAGE. See FIG. 3.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide which is at least 95% identical to a member selected from the group consisting of:

(a) a polynucleotide encoding a polypeptide comprising amino acids having the sequence set fort in SEQ ID NO: 2;

(b) a polynucleotide encoding a polypeptide comprising amino acid 1 to amino acid 214 as set forth in SEQ ID NO: 2; and (c) a polynucleotide complementary to the polynucleotide of (a) or (b).

2. The polynucleotide of claim 1 encoding a polypeptide comprising amino acids having the sequence set forth in SEQ ID NO:2.

3. A vector containing the polynucleotide of claim 2.

4. A host cell transfected with the polynucleotide of claim 2.

5. A process for producing a polypeptide comprising:

culturing the host cell of claim 4 under conditions suitable to produce the polypeptide encoded by said polynucleotide.

6. The isolated polynucleotide of claim 1 comprising a polynucleotide encoding a polypeptide comprising amino acid 1 to amino acid 214 as set forth in SEQ ID NO:2.

7. The polynucleotide of claim 1 comprising from nucleotide 1 to nucleotide 771 as set forth in SEQ ID NO:1.

8. The isolated polynucleotide of claim 1 comprising the nucleotides of SEQ ID NO: 1 encoding a polypeptide comprising amino acids 1 to 214 of SEQ ID NO:2.

9. The polynucleotide of claim 1 wherein the polynucleotide is DNA.

10. A vector containing the polynucleotide of claim 9.

11. A host cell transfected with the polynucleotide of claim 9.

12. A process for producing a polypeptide comprising:

culturing the host cell of claim 11 under conditions suitable to produce the polypeptide encoded by said polynucleotide.

13. The polynucleotide of claim 1 wherein the polynucleotide is RNA.

14. A vector containing the polynucleotide of claim 1.

15. A host cell transfected with the polynucleotide of claim 1.

16. A process for producing a polypeptide comprising:

culturing the host cell of claim 15 under conditions suitable to produce the polypeptide encoded by said polynucleotide.

17. An isolated polynucleotide comprising a polynucleotide having at least a 95 % identity to, a member selected from the group consisting of:

(a) a polynucleotide encoding a mature corpuscles of stannius polypeptide encoded by the DNA contained in ATCC Deposit No. 75652; and (b) a polynucleotide encoding a corpuscles of stannius polypeptide expressed by the DNA contained in ATCC Deposit No. 7565.

18. The isolated polynucleotide of claim 17 comprising a polynucleotide encoding a mature corpuscles of stannius polypeptide encoded by the DNA contained in ATCC Deposit No. 75652.

19. A vector containing the polynucleotide of claim 18.

20. A host cell transfected with the polynucleotide of claim 18.

21. A process for producing a polypeptide comprising:
   culturing the host cell of claim 20 under conditions suitable to produce the polypeptide encoded by said polynucleotide.

22. A vector containing the polynucleotide of claim 17.

23. A host cell transfected with the polynucleotide of claim 17.

24. A process for producing a polypeptide comprising:
   culturing the host cell of claim 23 under conditions suitable to produce the polypeptide encoded by said polynucleotide.

* * * * *

UNITED STATES PATENT AND TRADEMARK OFFICE
CERTIFICATE OF CORRECTION

PATENT NO. : 5,837,498
DATED : November 17, 1998
INVENTOR(S) : Henrik S. Olsen
Mark D. Adams It is certified that error appears in the above-identified patent and that said Letters Patent is hereby corrected as shown below:

On the title page:

Please correct item: [73] to read as follows:

Human Genome Sciences, Inc.,
    Rockville, Md.

Signed and Sealed this

Twenty-third Day of March, 1999

Attest:

Q. TODD DICKINSON

*Attesting Officer*    *Acting Commissioner of Patents and Trademarks*